United States Patent [19]

Hirayama et al.

[11] Patent Number: 5,064,529
[45] Date of Patent: Nov. 12, 1991

[54] APPARATUS FOR TESTING MEMBRANE FILTERS

[75] Inventors: Shigemitsu Hirayama, Yao; Takamichi Akashi, Ikeda; Akio Ikuta, Osaka; Isao Sasaki, Minoo; Hiroshi Fukuda, Tokyo, all of Japan

[73] Assignee: Fujisawa Pharmaceutical Co., Ltd., Osaka, Japan

[21] Appl. No.: 396,912

[22] Filed: Aug. 22, 1989

Related U.S. Application Data

[60] Division of Ser. No. 291,395, Dec. 27, 1988, Pat. No. 4,872,974, which is a continuation of Ser. No. 45,159, May 4, 1987, abandoned, which is a continuation of Ser. No. 647,886, Sep. 6, 1984, abandoned.

[30] Foreign Application Priority Data

Sep. 9, 1983 [JP] Japan ............................... 58-167343
Mar. 19, 1984 [JP] Japan ............................... 59-53259

[51] Int. Cl.$^5$ ...................... G01N 15/08; B01D 13/00
[52] U.S. Cl. ............................................ 210/90; 73/38; 210/140; 210/143; 210/321.69
[58] Field of Search ................. 73/38; 210/90, 92, 86, 210/140, 143, 436, 472, 636, 321.69

[56] References Cited

U.S. PATENT DOCUMENTS 4,449,392  5/1984  Huschke .............................. 73/40

FOREIGN PATENT DOCUMENTS 64159  3/1982  European Pat. Off. .

Primary Examiner—Karen M. Hastings
Attorney, Agent, or Firm—Oblon, Spivak, McClelland, Maier & Neustadt

[57] ABSTRACT

A membrane filter testing apparatus uses a control circuit for increasing the pressure at the primary side of a membrane filter fixedly accommodated in a housing and wetted with a liquid, by a gas at a predetermined rate, and checking whether the pressure at the primary side of the membrane filter is within a specified judging range after lapse of a predetermined period of time.

3 Claims, 5 Drawing Sheets

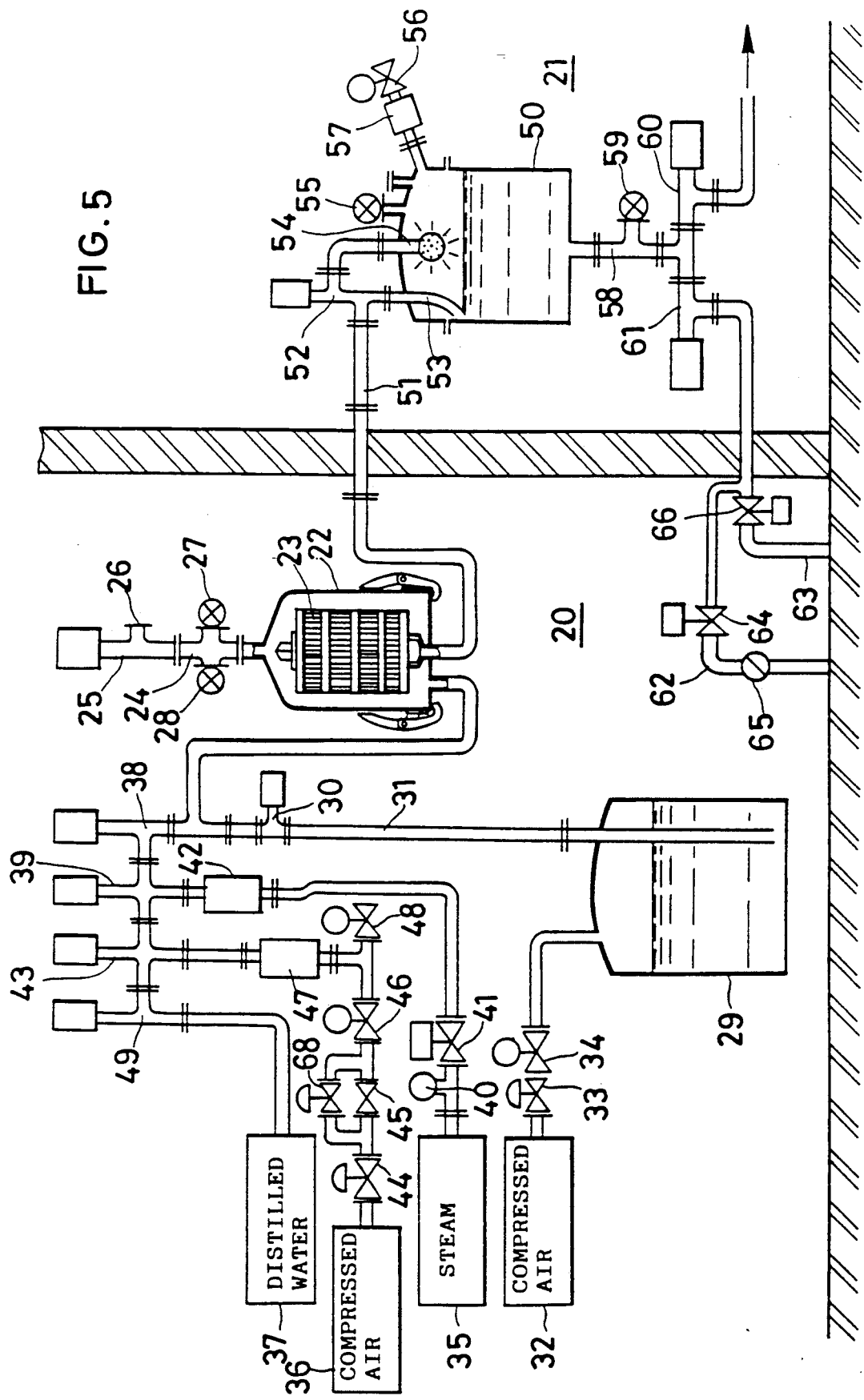

APPARATUS FOR TESTING MEMBRANE FILTERS

This application is a divisional application of U.S. Ser. No. 07/291,395, filed on Dec. 27, 1988, now U.S. Pat. No. 4,872,974, which is a file wrapper continuation application of U.S. Ser. No. 07/045,159, filed on May 4, 1987, now abandoned, which is a file wrapper continuation application of U.S. Ser. No. 06/647,886, filed on Sept. 6, 1984, now abandoned.

BACKGROUND OF THE INVENTION

The present invention relates to a method of and an apparatus for testing membrane filters, and an apparatus for sterilizing liquids with use of a membrane filter.

A filtration process for sterilizing liquids with use of membrane filters is needed for preparing injection solutions and other liquid pharmaceuticals or for sterilizing industrial water. This process requires testing of the membrane filter for perfection and removal of air from the filter housing. To carry out the liquid sterilizing filtration process automatically, the automation of the filter perfection test and the deaeration of the filter housing is essential, but extreme difficulties are encountered in automating these steps as will be described later.

A description will be given of the conventional sterilizing filtration process for pharmaceutical liquids, especially membrane perfection test and filter housing deaeration.

First in a substerilization chamber, a medicinal liquid is sent from a preparation container through a filter for rough filtration into a primary receptacle (container) which has been cleaned and sterilized. On the other hand, a secondary receptacle (container) cleaned for containing the sterilized filtrate and a filter housing are placed into a sterilization chamber through a sterilizer provided between the substerilization chamber and the sterilization chamber. The filter housing has enclosed therein a cartridge membrane filter and is provided with tubes connected to the primary side and the secondary side of the filter.

The membrane filter is tested for perfection in the sterilization chamber. The bubble point test (hereinafter referred to as "BPT") standardized according to ASTM-F316-70 is widely used as a method of testing membrane filters without entailing breaking or contamination and with ease and good reproducibility. According to BPT, the pores of the filter are regarded as capillary tubes, and the maximum radius of the pores is determined by measuring pressure, based on the relationship between the pressure and the maximum pore radius expressed by the equation (I) of surface tension given below. Conventionally this test is carried out in the following manner. First, the primary-side tube of the filter housing is connected to a gas source, such as an air, nitrogen or carbon dioxide source, via an indicating pressure gauge and a ball valve, while the forward end of the secondary-side tube of the housing is placed into water in a container. Prior to testing, the filter is impregnated with a liquid, such as distilled water, to fill the filter pores with the liquid by capillarity. With the valve opened to a suitable extent, the primary side of the filter is gradually pressurized with the gas. While checking the housing for leakage with the unaided eye, the operator observes the pressure gause and the end of the secondary-side tube. While the gas pressure applied to the primary side of the filter is relatively low, the pressure remains in an equilibrium with the liquid in the filter pores, so that the displacement of the liquid from the pores is negligible. When the pressure reaches a level, the liquid in large pores is forced out from the pores toward the primary side: This can be recognized from bubbles released from the end of the secondary-side tube. The pressure at this time is taken as bubble point pressure (hereinafter referred to as "BP pressure"). The relationship between this pressure P and the maximum radius r of filter pores is expressed by the following surface tension equation (I):

$$r = k(2\sigma \cos \theta / P) \quad \text{(I)}$$

where $\sigma$ is surface tension, $\theta$ is contact angle, and k is a shape correction factor. Accordingly the filter pore size can be calculated from the BP pressure measurement as above. With the above method, however, it is necessary for the operator to observe the pressure gauge and the tube end at all times until the secondary-side tube releases bubbles and to read the pressure upon the release of bubbles. The procedure is therefore very cumbersome and involves extreme difficulties in automation. Further apparatus proposed for automatically testing membrane filters for perfection include one which is adapted to measure the rate of flow of diffused gas toward the secondary side of the filter when a pressure of about 80% of the BP pressure is applied to its primary side, or one which is adapted to detect the BP pressure reached by intermittently applying pressure to the primary side of the filter and measuring the variations in the pressure. The former apparatus nevertheless has the problem that the measurement varies with the filtering area of the filter and involves a greater error in the case of smaller filters. The latter apparatus has the problem that the measuring condition differs with the capacity of the housing. In either case, the delicate test condition setting needed renders the apparatus complex, expensive and difficult to maintain. Further although the test itself is conducted automatically, the acceptability of the filter as to its perfection must be determined by the operator based on the measurement. Accordingly it is extremely difficult to incorporate such a conventional apparatus into a line as an in-line filter testing apparatus.

When the perfection test for the membrane filter is completed, the primary-side tube of the filter housing is passed through the wall between the substerilization chamber and the sterilization chamber and is connected to the primary receptacle in the former chamber, and the secondary tube is connected to the secondary receptacle in the sterilization chamber to remove air from the housing, i.e. to discharge air from the primary side of the filter to ensure the filtering area of the filter. This is done by sending the medicinal liquid from the primary receptacle to the primary side of the housing, with the upper end of the housing held open. When the medicinal liquid is sent to the primary side of the housing, the air therein is discharged from the upper end of the housing, allowing the liquid level to gradually rise within the housing. While observing the liquid level, the operator closes the housing upper end upon the liquid level passing over the filter to complete deaeration. Thus, it is necessary for the operator to observe the liquid level within the housing at all times also during deaeration, so that the procedure is cumbersome and very difficult to automate.

After the filter housing is completely deaerated, the medicinal liquid is passed from the primary receptacle to the secondary receptacle continuously through the filter within the housing thus deaerated, whereby the liquid is sterilized by filtration.

When the medicinal liquid in one primary receptacle is completely filtered in this way, the primary and secondary receptacles are disconnected from the tubes of the filter housing. The secondary receptacle containing the sterilized liquid is carried to a filling machine within the sterilization chamber for filling. Before other primary and secondary receptacles are used for sterilizing medicinal liquid, membrane filter perfection test and filter housing deaeration must be carried out manually as above. The medicinal liquid may be sterilized and filled at the same time with use of a buffer tank connected to the filling machine, in place of the secondary receptacle. Even in this case, the membrane filter perfection test and filter housing deaeration must be conducted manually as above every time the liquid in one primary receptacle has been sterilized.

SUMMARY OF THE INVENTION

An object of the present invention is to provide a method of testing membrane filters for perfection easily and accurately and an apparatus for practicing this method.

Another object of the invention is to provide a filtration apparatus for sterilizing liquids automatically with savings in labor.

The membrane filter testing method of this invention is characterized by increasing the pressure of primary side of a membrane filter, fixedly enclosed in a housing and wetted with a liquid, by a gas at a predetermined rate, and checking after lapse of a predetermined period of time whether the pressure of the primary side of the membrane filter is within a specified judging range.

The membrane filter testing apparatus of the present invention is characterized in that the apparatus comprises a gas source connectable to the primary side of a membrane filter fixedly enclosed in a housing and wetted with a liquid, pressure increase rate setting means positionable between the gas source and the primary side of the membrane filter to maintain the rate of increase of the pressure at the primary side of the membrane filter by the gas at a specified value, and a pressure sensor positionable at the primary side of the membrane filter.

We have carried out research on the membrane filter perfection test and accomplished the present invention based on the following finding. When the pressure of the primary side of a flawless filter wetted with a liquid is increased at a predetermined rate by a gas, the amount of supply of the gas from the primary side remains in an equilibrium with the amount of discharge of the gas to the secondary side after the primary side has reached the BP pressure, so that the pressure of the primary side is maintained at a constant level. In this case, the time taken for the pressure of the primary side of the flawless filter to reach the BP pressure is substantially definite and is dependent on the BP pressure of the filter and the rate of increase of the pressure. Accordingly the filter can be tested for perfection easily and accurately by checking whether the primary-side pressure is within a specified judging range after the lapse of a predetermined period of time which is longer than the above-mentioned time. Experiments have shown that the perfection of filters can be determined quantitatively with no error between the measurement thus obtained and the measurement obtained by the conventional BPT method. The pressure may be checked by the operator with reference to a pressure gauge after the lapse of the predetermined period of time, or to a recorder which records the primary-side pressure until the predetermined period elapses. Alternatively, the pressure may be checked by automatic means after the lapse of the time period.

The test method of the invention can be conducted merely by increasing the pressure of the primary side of a membrane filter, fixedly enclosed in a housing and wetted with a liquid, by a gas at a predetermined rate and checking whether the primary-side pressure is within a specified judging range after the lapse of a predetermined period of time. Accordingly the primary-side pressure need not always be monitored during the rise of pressure, and yet the filter can be tested for perfection with ease and accuracy. Thus, even when the pressure is checked by the operator, the pressure gauge and the bubble detecting tube end need not be observed at all times unlike the conventional practice. This greatly lessens the burden on the operator. Further when the pressure is checked by automatic means, the pressure after the lapse of the predetermined time period need to be compared only with the upper and lower limits of the judging range. This greatly simplifies the construction of the apparatus, especially that of electronic circuit for automatic control and checking. The present invention further facilitates in-line testing because a gas source and a pressure sensor only are connected to the primary side of the housing and there is no need to connect the bubble detecting tube, conventionally used to the secondary side. The present test apparatus has a simple construction including a gas source, pressure increase rate setting means and pressure sensor and is also greatly simplified in its electronic circuit as mentioned above. The apparatus is therefore inexpensive to make, easy to maintain and also easy to incorporate into a line an as in-line automatic tester.

When the primary-side pressure of the membrane filter is increased, it is desirable to interrupt the increase of the pressure for a predetermined period of time upon the primary-side pressure reaching a predetermined level lower than the lower limit of the judging range and to check whether the primary-side pressure decreases during the interruption. It is then possible to check the housing and the piping system for improper sealing and the filter for inadequate wetting.

The present invenion provides a liquid sterilizing filtration apparatus comprising a filter housing for fixedly accommodating a membrane filter therein, a primary container for containing a prefilt, a primary pipe connecting the primary side of the filter housing to the primary container, a secondary container for containing a filtrate, and a secondary pipe connecting the secondary side of the filter housing to the secondary container, the apparatus being characterized in that a steam source, a gas source and a distilled water source are connected to the primary pipe via a change-over valve, pressure increase rate setting means being provided between the gas source and the change-over valve for maintaining the rate of increase of the pressure at the primary side of the membrane filter by a gas at a predetermined value, an air outlet being provided at an upper portion of the filter housing and openable by a valve, a pressure sensor being provided at the primary side of the filter housing.

The filtration apparatus of the present invention is adapted to automatically test a membrane filter for perection in a process for sterilizing a liquid by filtration, so that the liquid can be sterilized automatically at a reduced cost, with savings in labor and with improved reliability.

The invention further provides a liquid sterilizing filtration apparatus comprising a filter housing for fixedly accommodating a membrane filter therein, a primary container for containing a prefilt, a primary pipe connecting the primary side of the filter housing to the primary container, a secondary container for containing a filtrate, and a secondary pipe connecting the secondary side of the filter housing to the secondary container, the apparatus being characterized in that a steam source, a gas source and a distilled water source are connected to the primary pipe via a change-over valve, pressure increase rate setting means being provided between the gas source and the change-over valve for maintaining the rate of increase of the pressure at the primary side of the membrane filter by a gas at a predetermined value, an air outlet being provided at an upper portion of the filter housing and openable by a valve, a liquid level sensor being provided on the filter housing and positioned above the membrane filter, a pressure sensor being provided at the primary side of the filter housing.

The filtration apparatus of the invention is adapted for automatic membrane perfection testing and also for automatic removal of air from the filter housing, whereby liquid sterilizing filtration can be automatically carried out with improved efficiency.

Other features of the present invention will become apparent from the following description.

BRIEF DESCRIPTION OF THE DRAWINGS

FIG. 5 is a diagram showing the piping system of a medicinal liquid sterilizing filtration apparatus embodying the invention;

DESCRIPTION OF THE PREFERRED EMBODIMENTS

Figure 1:
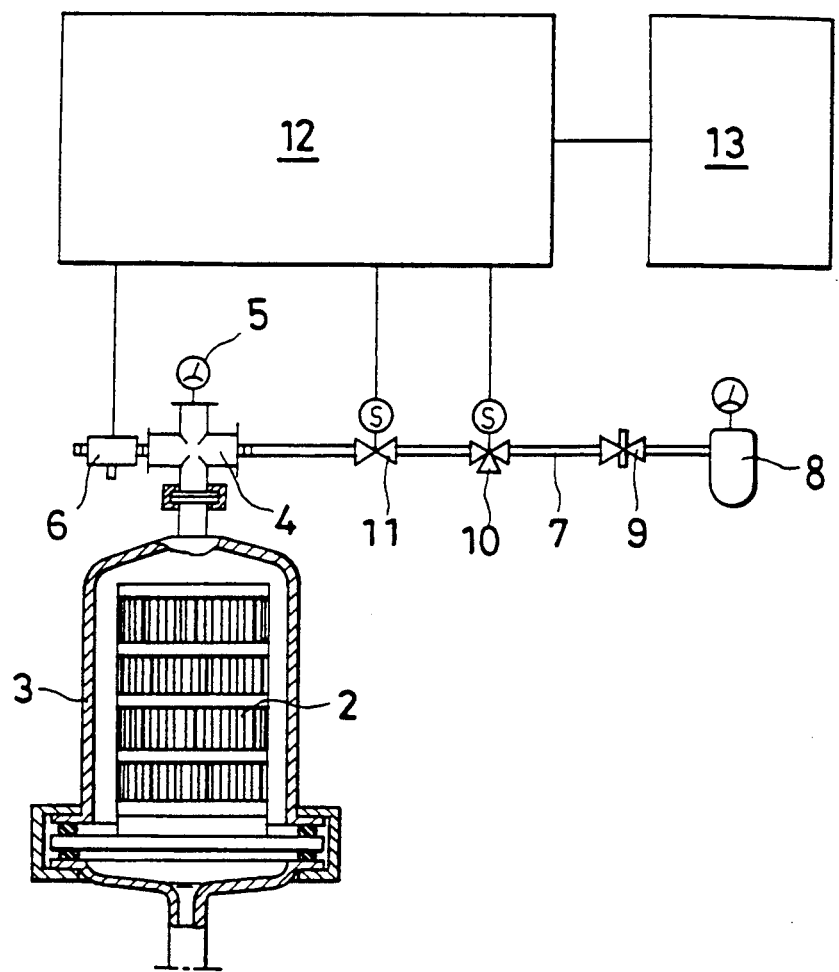
FIG. 1 is a diagram showing the piping system of a membrane filter testing apparatus embodying the invention.

FIG. 1 shows an off-line testing apparatus which is not incorporated into a line. The apparatus is connected in the following manner to the primary side of a housing 3 accommodating a cartridge membrane filter 2 therein. One end of a cross joint 4 is joined to the primary side of the housing 3. An indicating pressure gauge and a pressure sensor 6 which comprises a strain gauge or the like are connected to other two ends of the joint 4. A gas source 8 is connected to the remaining end of the joint 4 by a pipe 7. Mounted on the pipe 7 are a pressure increase rate setting valve 9 comprising a needle valve, a three-way electromagnetic valve (three-way valve) 10 and a two-way electromagnetic valve (two-way valve) 11 which are arranged from the gas source 8 toward the joint 4 in the order mentioned. The three-way valve 10 has one port which is held open to the atmosphere. The pressure sensor 6, the three-way valve 10 and the two-way valve 11 are connected to a control circuit 12, which has connected thereto an automatic recorder 13.

The operation of the testing apparatus will be described below with reference to a case wherein a membrane filter having a pore size of 0.2 micron is tested for perfection. Flawless hydrophilic membrane filters of cellulose ester, nylon 6/6 or polyvinylidene fluoride, which are 0.2 micron in pore size, are about 3.5 kg/cm$^2$ in BP pressure.

Before testing, the two-way valve 11 is closed, and the three-way valve 10 is so set as to pass a gas therethrough from the setting valve 9 toward the two-way valve 11. Further prior to testing, the operator opens the setting valve 9 to a degree to give a predetermined rate of increase of pressure, i.e. 1 kg/cm$^2$ per second. A filter 2 wetted with a liquid is placed in the housing 3.

Figure 4:
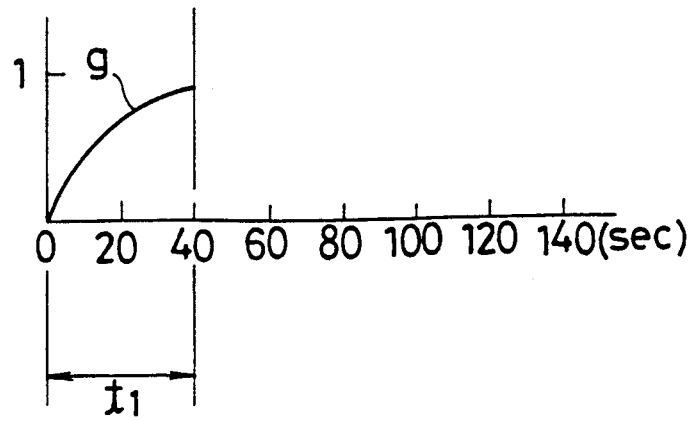
FIGS. 2, 3 and 4 are graphs respectively showing three examples of results obtained by testing membrane filters.
Figure 2:
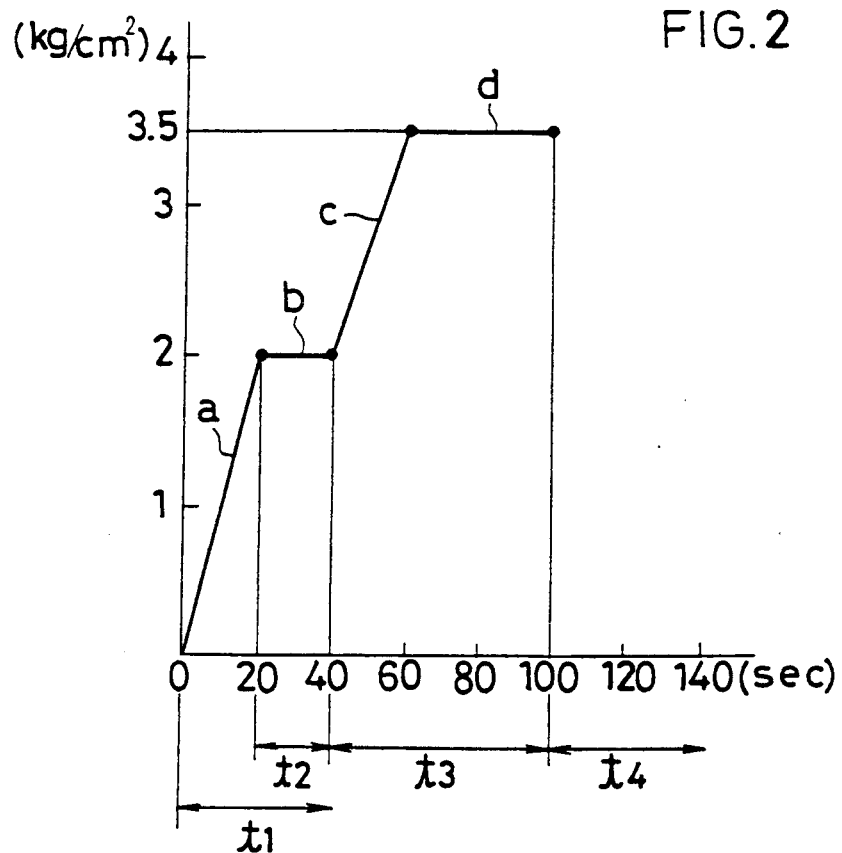
Figure 3:
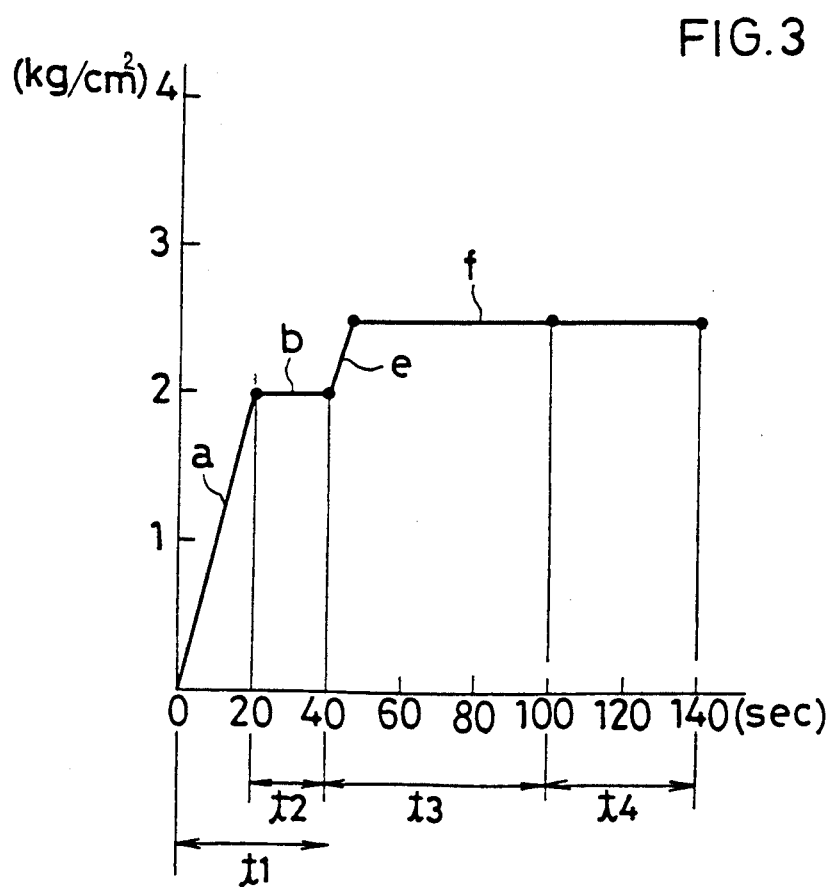

When the start switch is depressed in this state, the filter is tested automatically in the following manner, and the pressure at the primary side of the housing 3 automatically detected by the sensor 6 during testing is recorded on the recorder 13 as seen in FIGS. 2 to 4, in which the time (second) is plotted as abscissa vs. the primary-side pressure (kg/cm$^2$) of the housing 3 as ordinate.

Upon depression of the start switch, the two-way valve 11 is opened first, permitting supply of gas from the gas source 8 to the primary side of the housing 3. When the filter 2 is free from flaws and properly installed, the primary-side pressure increases at the above-mentioned rate as represented by straight line a in FIGS. 2 and 3. When the pressure increases to 2 kg/cm$^2$, the two-way valve 11 is closed to interrupt the increase of pressure for a predetermined period of time (t2=20 seconds). If the housing 3 or the piping is improperly sealed or the filter 2 is improperly wetted, the primary-side pressure decreases from 2 kg/cm$^2$ during the interruption, so that an alarm is given to interrupt the test. In the absence of such an abnormality, the primary-side pressure remains at a constant level as indicated by straight line b in FIGS. 2 and 3, and upon lapse of the time t2, the two-way valve 11 is opened to resume increase of pressure. A predetermined period of time (t3=60 seconds) after the resumption of pressure increase, the primary-side pressure is automatically checked as to whether it is in a specified judging range (3.5±0.5 kg/cm$^2$).

When the filter is flawless and 0.2 micron in pore size, the primary-side pressure increases at the foregoing rate after the resumption of pressure increase as indicated by straight line c in FIG. 2, and is maintained at a constant level as indicated by straight line d in FIG. 2 after reaching the BP pressure (3.5 kg/cm$^2$). Since the pressure (3.5 kg/cm$^2$) obtained upon lapse of the time t3 after the restart of pressure increase is within the judging range of 3.5±0.5 kg/cm$^2$, the filter is found to be normal, a normality lamp is turned on, and the three-way valve 10 is operated to discharge air from the primary side of the housing 3 into the atmosphere via the valve 10, whereby the test is completed.

If the filter is larger than 0.2 micron in pore size, for example, when a filter having a pore size of 0.45 micron is installed by mistake, the primary-side pressure increases at the above rate after the restart of pressure increase as indicated by straight line e in FIG. 3 and remains constant after reaching a BP pressure of 2.4 kg/cm$^2$ as indicated by straight line f in FIG. 3. The pressure (2.4 kg/cm$^2$) obtained upon the lapse of the above-mentioned time t3 after the restart of pressure increase is lower than the lower limit (3 kg/cm$^2$) of the judging range, so that a judgment of abnormality is given, the alarm goes on, and then the pressure is further maintained for a predetermined period of time (t4=40 seconds) to clearly identify the abnormality. In the same manner as above, the gas is discharged from the primary side to complete the test.

Conversely, when the filter is smaller than 0.2 micron in pore size, for example, when a filter having a pore size of 0.1 micron (BP pressure: 17 kg/cm$^2$) is installed by mistake, the pressure upon lapse of the time t3 after the resumption of pressure increase is higher than the upper limit (4 kg/cm$^2$) of the judging range, with the result that a judgment of abnormality is given, and the alarm goes on to complete the test.

If the filter has a flaw or is improperly installed, the primary-side pressure increases as indicated by curve g in FIG. 4 after the initiation of increase of pressure. The pressure fails to reach 2 kg/cm$^2$ even after the lapse of the predetermined time (t1=40 seconds) after the start of pressure increase. Consequently a judgment of abnormality is given, the alarm goes on, and the gas is discharged from the primary side as stated above, whereby the test is completed.

Although the apparatus and method according to the foregoing embodiment are adapted for off-line testing, it is of course possible to incorporate such an apparatus into a line for in-line testing. More specifically, in-line tests can be carried out automatically in sterilized state with use of the sterilizing filtration system presently employed at plants, by incorporating the pressure sensor alone into the line within a sterilization chamber. In this case, the test results obtained in the entire plant can be concentrically monitored or recorded at one location. Further it is possible to incorporate the pressure sensor into the primary side of a housing for a plurality of filters which are repeatedly used for a long period of time, for example, final filters for bottle washer finishing water or air-vent filters for distilled water tanks, and to use the other components of the apparatus commonly for these filters, whereby periodic tests can be conducted automatically within a short period of time without disassembling the line.

FIG. 5 shows a sterilizing filtration apparatus including a membrane filter for automatic filling equipment for a medicinal liquid. The apparatus has incorporated therein an in-line automatic tester for the membrane filter and comprises the following components which are disposed in a substerilization chamber 20 and a sterilization chamber 21.

A filter housing 22 installed in the substerilization chamber 20 has a cartridge membrane filter 23 fixedly accommodated therein. A remote control air discharge valve 25 is connected to the upper end of the filter housing 22 by an air discharge pipe 24. The air discharge valve 25 has an air outlet 26 which is thereby opened or closed. The air discharge pipe 24 is provided with a liquid level sensor 27 comprising an optical fiber 67, and a pressure sensor 28. The membrane filter 23 and the filter housing 22 per se have the same construction as those already known.

A preparation container (primary container) 29 for containing the medicinal liquid to be filtered is disposed in the substerilization chamber 20. The container 20 is connected to the primary side of the filter housing 22 by a primary pipe 31 having a first remote control change-over valve 30. A first compressed air source 32 is provided in the substerilization chamber 20 for forcibly sending the medicinal liquid from the container 29 to the primary side of the housing 22 via the primary pipe 31. A sixth remote control change-over valve 33 and a first regulating valve 34 are provided between the compressed air source 32 and the preparation container 29.

Further disposed in the chamber 20 are. a steam source 35 for steam sterilization, a second compressed air source (gas source) 36 for air blowing and for testing the membrane filter 23 for perfection, and a distilled water source 37 for rinsing and for membrane perfection testing. The steam source 35 is connected, by way of a second remote control change-over valve 38 and a third remote control change-over valve 39, to a portion between the filter housing 22 and the first change-over valve 30 on the primary pipe 31. A pressure gauge 40, a seventh remote control change-over valve 41 and a filter 42 are provided between the steam source 35 and the third change-over valve 39. By way of a fourth remote control change-over valve 43, the second compressed air source 36 is connected to the third change-over valve 39. Provided between the air source 36 and the fourth valve 43 are an eighth remote control change-over valve 44, a pressure increased rate setting valve 45 comprising a needle valve, a second regulating valve 46 and a filter 47. A ninth remote control change-over valve 68 is disposed in parallel with the valve 45, and an air discharge valve 48 is provided between the regulating valve 46 and the filter 47. The distilled water source 37 is connected to the fourth change-over valve 43 via a fifth remote control change-over valve 49.

A buffer tank (secondary container) 50 for temporarily containing the filtered medicinal liquid is provided in the sterilization chamber 21. The secondary side of the filter housing 22 is connected to the tank 50 by a secondary pipe 51 extending from the chamber 20 into the chamber 21. Via a tenth remote control change-over valve 52, a medicinal liquid inlet pipe 53 and a fluid discharge pipe 54 are connected in parallel with the pipe 51 within the chamber 21. The forward end of the inlet pipe 53 is opposed to an upper inside wall surface of the tank 50, while the lower end of the discharge pipe 54 is positioned at an upper interior portion of the tank 50 centrally thereof. A temperature sensor 55 is provided on the top of the tank 50, and an air discharge valve 56 is connected to an upper portion of the tank 50 via a filter 57. A medicinal liquid outlet pipe 58 connected to the bottom of the tank 54 has a liquid level sensor 59 which is adapted to detect the liquid level within the tank 50 by the liquid pressure. The outlet pipe 58 is connected to a filling machine (not shown) via an eleventh remote control change-over valve 60 and to a steam discharge pipe 62 and a drain pipe 63 via a twelfth remote control change-over valve 61. The pipes 62 and 63 are disposed in the chamber 20. The steam discharge pipe 62 has a thirteenth remote control change-over valve 64 and a steam trap 65. The drain pipe 63 has a fourteenth remote control change-over valve 66.

Figure 10:
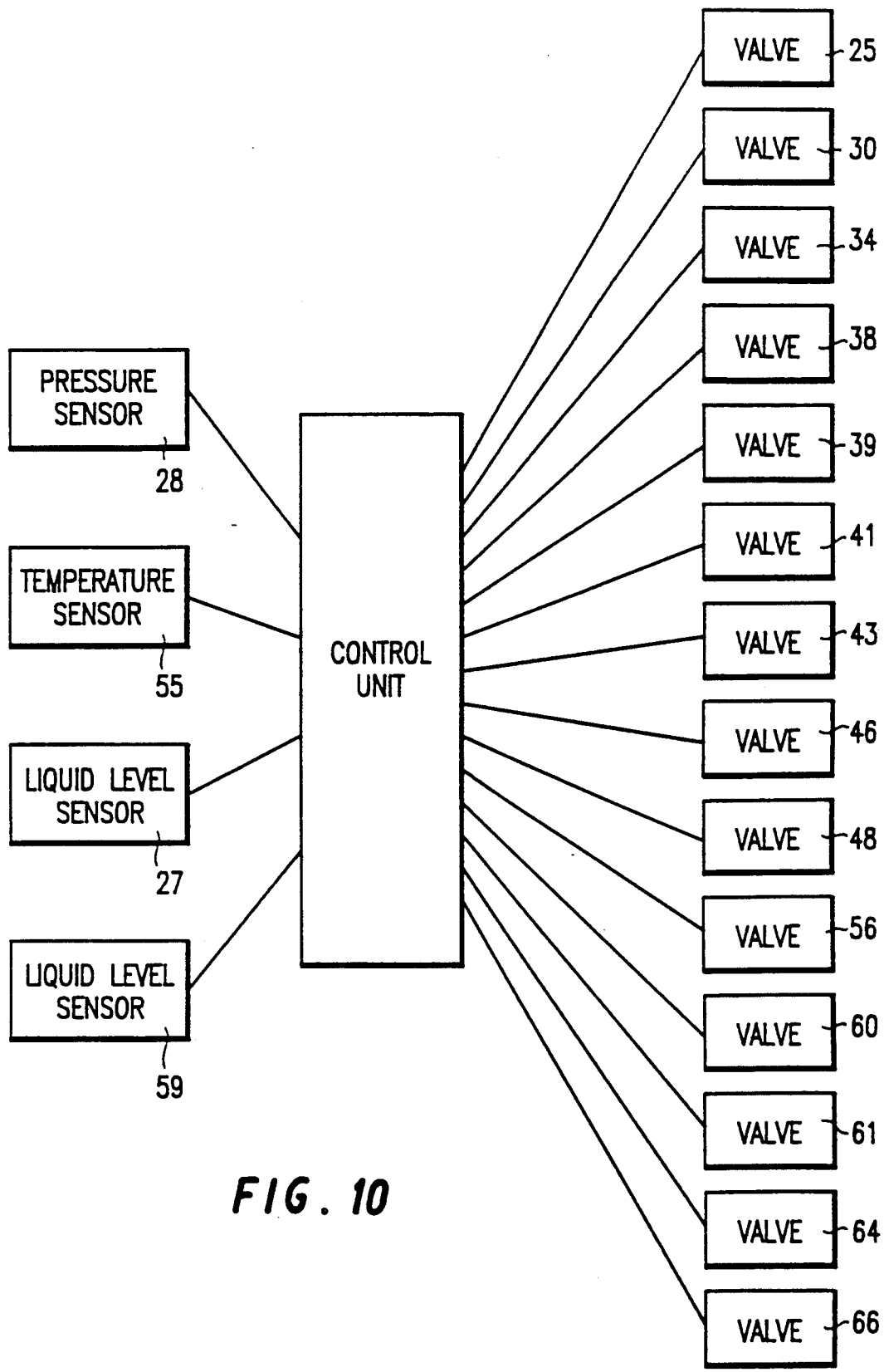
FIG. 10 is a block diagram of the control unit, sensors and valves.

In FIG. 10, illustrating control unit, sensors and valves, pressure sensor 28 controls the valves 46, 48, 43 and 38 when testing bubble point, and the valves 34, 30 and 60, respectively, when conducting filtration; temperature sensor 55 controls the valves 41, 39, 38, 56, 61, 64 and 66 when performing sterilization; liquid level sensor 27 controls the valve 25 on filtering, and liquid level sensor 59 controls the valves 34 and 30 on filtering. The control unit is designed in such a manner that the acceptability of a filter is automatically judged as to its perfection by evaluating whether the pressure at the primary side of the membrane filter is within a specified judging range at a predetermined time after the start of increase of the pressure at the primary side of the membrane filter by the gas.

As not shown, the filling equipment is provided with a control unit comprising a microcomputer for controlling the overall equipment to automatically sterilize and fill the medicinal liquid, for example, in the following manner.

First for steam sterilization, the valves concerned are controlled so that steam flows from the steam source 35 into the steam discharge pipe 62 through the third and second change-over valves 39, 38, the primary pipe 31, the membrane filter 23 within the housing 22, the secondary pipe 51, the tenth change-over valve 52, the liquid inlet pipe 53 and the fluid discharge pipe 54, the buffer tank 50, the liquid outelt pipe 58 and the twelfth change-over valve 61. At this time, the air discharge valve 25 for the housing 22 and the air discharge valve 56 for the buffer tank 50 are both held closed. During the steam sterilization, the temperature of steam is monitored by the temperature sensor 55 on the buffer tank 50, such that the opening of the seventh change-over valve 41 for the steam source 35 is controlled to obtain the desired temperature.

Next, air is passed from the second compressed air source 36 into the drain pipe 63 through the ninth change-over valve 68, the fourth, third and second change-over valves 43, 39, 38, the primary pipe 31, the membrane filter 23 within the housing 22, the secondary pipe 51, the tenth change-over valve 52, the liquid inlet pipe 53 and the fluid discharge pipe 54, the buffer tank 50, the liquid outlet pipe 58 and the twelfth change-over valve 61, by controlling the valves concerned. The air thus blown in removes the remaining condensed water from the components and cools the membrane filter 23. At this time, the air discharge valve 25 for the filter housing 22 is held closed, but the air discharge valve 56 for the buffer tank 50 is open to a suitable degree. During the air blowing, the temperature of air, i.e. the temperature of the membrane filter 22, is monitored by the temperature sensor 55 on the buffer tank 50, such that the supply of air is discontinued when the temperature drops to the desired level.

To rinse the apparatus, distilled water is then passed from the distilled water source 37 into the drain pipe 63 through the fifth, fourth, third and second control valves 49, 43, 39, 38, the primary pipe 31, the membrane filter 23 within the housing 22, the secondary pipe 51, the tenth change-over valve 52, the liquid inlet pipe 53 and the fluid discharge pipe 54, the buffer tank 50, the liquid outlet pipe 58 and the twelfth change-over pipe 61, by controlling the valves concerned. The components are rinsed and the membrane filter 23 is wetted with the distilled water. At this time, the air discharge valve 25 for the housing 22 is held closed, but the air discharge valve 56 for the buffer tank 50 is open to a suitable degree.

Air is thereafter caused to flow from the second compressed air source 36 into the drain pipe 63 via the pressure increase rate setting valve 45, the fourth, third and second change-over valves 43, 39, 38, the primary pipe 31, the membrane filter 23 within the housing 22, the secondary pipe 51, the tenth change-over valve 52, the liquid inlet pipe 53 and the fluid discharge pipe 54, the buffer tank 50, the liquid outlet pipe 58 and the twelfth change-over valve 61, by controlling the valves concerned, whereby the membrane filter 23 is tested for perfection.

The test is carried out generally in the same manner as is the case with the test apparatus of FIG. 1.

Before the start of the membrane filter perfection test, the eighth change-over valve 44 for the second compressed air source 36 is closed. Prior to testing, the setting valve 45 is adjusted by the operator to a predetermined pressure increase rate. During testing, the air discharge valve 25 for the housing 22 is held closed, but the air discharge valve 56 for the buffer tank 50 is open to a suitable degree.

In this state, the eighth change-over valve 44 is first opened to start testing, causing the second compressed air source 36 to supply air to the primary side of the housing 22 through the setting valve 45.

If the housing 22 or the piping system is sealed improperly or the filter 23 is wetted improperly, an alarm is given, and the test is discontinued as is the case with the apparatus of FIG. 1. Further when the filter is larger than 0.2 micron in pore size, e.g. when a filter having a pore size of 0.45 micron is installed by mistake, or if the filter is smaller than 0.2 micron in pore size, e.g. if a filter having a pore size of 0.1 micron is installed by mistake, an alarm is given, whereupon the test is discontinued. Further when the filter has a defect or is improperly installed, an alarm is given, whereupon the test is discontinued.

Figure 6:
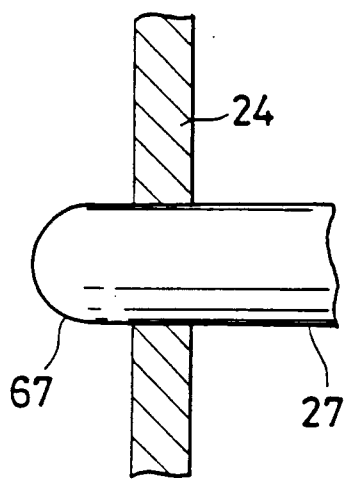
FIG. 6 is an enlarged side elevation showing the main portion of a liquid level sensor in FIG. 5.

When the membrane filter is completely tested and found to be normal, valves are so controlled as to cause the first compressed air source 32 to send air into the preparation container 29, such that the resulting pressure will cause the medicinal liquid to flow from the container 29 into the filling machine by way of the membrane filter 23 within the housing 22, the secondary pipe 51, the tenth change-over valve 52, the liquid inlet pipe 53, the buffer tank 50, the liquid outlet pipe 58 and the eleventh change-over valve 60. In this state, air is removed from the filter housing 22 first, and the medicinal liquid is then filtered for sterilization. In the meantime, the air discharge valve 56 for the buffer tank 50 is held open to a suitable degree, while the air discharge valve 25 for the housing 22 is opened before the start of deaeration or venting of the filter housing 22. When the medicinal liquid is supplied to the housing 22 via the primary pipe 31 in this state, the air at the primary side of the housing is forced out from the air outlet 26 via the air discharge pipe 24 and valve 25, permitting the liquid level within the housing 22 to rise gradually. When the liquid level reaches the liquid level sensor 27, this is detected in the following manner, whereupon the air discharge valve 25 is closed to complete the removal of air. With reference to FIG. 6, the forward end of the optical fiber 67 constituting the liquid level sensor 27 is positioned slightly inside the air discharge pipe 24, such that the light transmitted through the optical fiber is partially reflected at the forward end and returned through the fiber. The reflectance of light at the end of the optical fiber 67 differs depending on whether the liquid level is below or at the fiber end, i.e. whether the fiber end is exposed to air or the medicinal liquid. Thus, the amount of returning light varies, and the liquid level reaching the optical fiber 67 is detected by the variation. The liquid level sensor 27 comprising the optical fiber 67 has very high responsiveness, so that the discharge valve 25 can be closed immediately when the liquid level reaches the sensor 27. Air may be removed from the filter housing 22 manually as heretofore done.

When the filter housing 22 has been completely vented with the closing of the air discharge valve 25, the medicinal liquid is sterilized by filtration in the same state. The liquid sent from the preparation container 29 to the primary side of the filter housing 22 through the primary pipe 31 is filtered by the membrane filter 23, flows to the secondary side and enters the buffer tank 50 via the secondary pipe 51 and the liquid inlet pipe 53. Four liquid levels are set for the buffer tank 50; i.e. an allowable lower limit, a reference lower limit, a reference upper limit, and an allowable upper limit, as arranged in the ascending order. The eleventh change-over valve 60 is held closed immediately after the start of filtration, and when the liquid level within the tank 50 reaches the reference upper limit, the valve 60 opens, whereby the liquid in the tank 50 is fed to the filling machine via the outlet pipe 58 and the valve 60. The rate of supply of the medicinal liquid to the tank 50 from the inlet pipe 53 is adjusted to a value slightly larger than the rate of discharge of the liquid from the outlet pipe 58, so that when the liquid level reaches the reference upper limit, the first change-over valve 30 closes to interrupt filtration. When the liquid level within the tank 50 lowers to the reference lower limit, the first change-over valve 30 opens to resume filtration. In this way, the liquid level within the tank 50 is maintained between the reference upper and lower limits during filtration.

When the liquid within the preparation container 29 has been wholly sent to the filter housing 22 and filtered, the container 29, the primary pipe 31 and the primary side of the housing 22 are full of air. However, this air, having a pressure lower than the BP pressure, will not pass through the filter 23, permitting the membrane filter to remain wet with the medicinal liquid. The filtrate is entirely sent to the tank 50 under gravity, and the liquid level within the tank 50 gradually lowers. The eleventh change-over valve 60 is closed to finish filtration immediately when the liquid level reaches the allowable lower limit or a predetermined period of time thereafter. When no medicinal liquid remains in the preparation container 29 at this time, this indicates that the filtration has been completed normally. If some medicinal liquid remains in the container 29 when the liquid level within the tank 50 lowers to the allowable lower limit, the remainder is interpreted as indicating an abnormality occurring somewhere in the apparatus, and an alarm is given. The liquid level reaching the allowable upper limit within the tank 50 is also interpreted as being indicative of an abnormality, and an alarm is given.

After the completion of filtration, the membrane filter 23 is tested again for perfection in order to check whether the filter 23 has functioned normally. Since the membrane filter 23 is wet with the medicinal liquid at this time as stated above, apparatus operates in the same manner as when distilled water is used although values are different.

When the membrane filter perfection test is completed, the filter 23 is manually removed from the housing 22, and the apparatus is cleaned with distilled water in the same manner as when distilled water is used for rinsing previously. At this time, a washing agent, organic solvent or the like may be used in place of distilled water.

Finally, the apparatus is dried in the same manner as the previous air blowing to complete the sterilizing filtration operation.

Although the membrane filter 23 is tested for perfection only before and after filtration, the filter can be so tested with use of the medicinal liquid in the same manner as above at a suitable time during filtration, for example, during interruption following the rise of the liquid level to the reference upper limit within the tank 50, whereby improved reliability is achieved.

Figure 7:
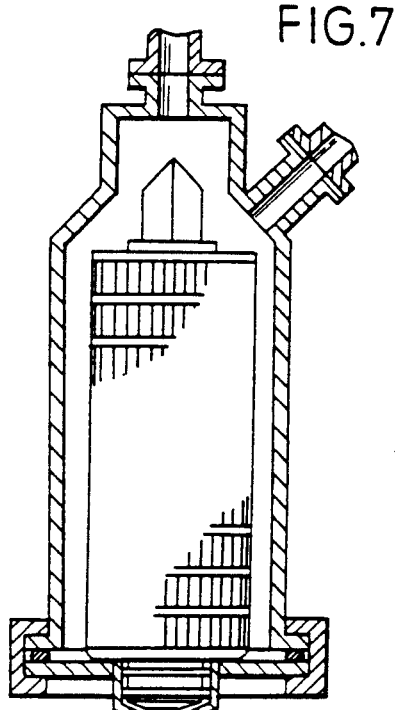
FIGS. 7, 8 and 9 are views in vertical section showing different modifications of the membrane filter and the filter housing shown in FIG. 5.
Figure 8:
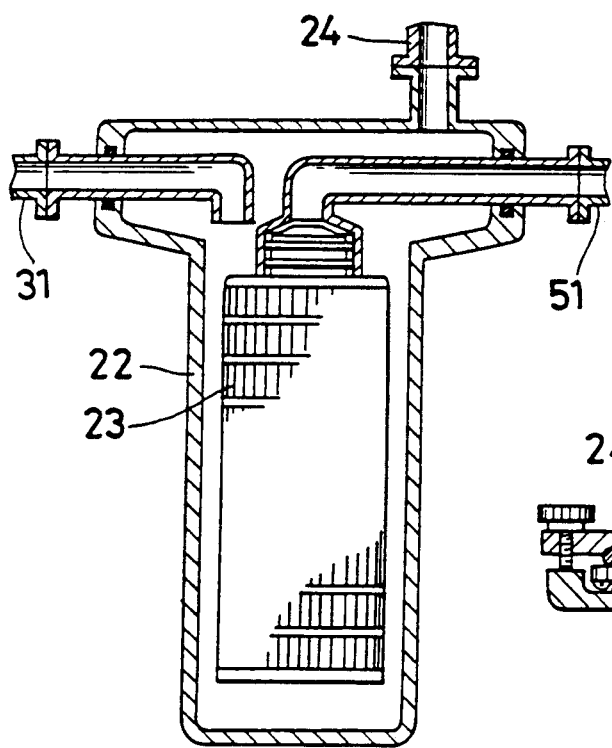
Figure 9:
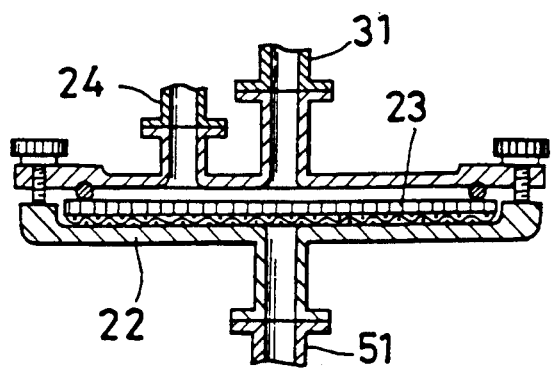

The membrane filter 23 and the housing 22 are not limited to those of the foregoing embodiment in construction but can be modified suitably. FIGS. 7 and 8 show different housings 22 for cartridge membrane filters 23, while FIG. 9 shows a disk-like membrane filter and a housing 22 therefor. Throughout the drawings showing filters and housings, like parts are referred to by like reference numerals. Further the membrane filter 23 may be tested for perfection with use of a suitable gas other than air.

The sterilizing filtration apparatus need not always be connected directly to the filling machine unlike the foregoing embodiment. The present invention is of course applicable to liquids other than medicinal liquids. The medicinal liquid sterilizing filtration apparatus described above is merely an embodiment of the invention, and the invention is of course not limited thereto.

What is claimed is:

1. A membrane filter testing apparatus, comprising a gas source connected to a primary side of a membrane filter fixedly accommodated in a housing and wetted with a liquid, a pressure sensor positioned at the primary side of the membrane filter, a valve positioned between the gas source and the primary side of the membrane filter to maintain a constant rate of pressure increase at the primary side of the membrane filter by the gas in a control circuit structured and arranged for controlling and detecting the gas pressure, wherein the control circuit comprises means for automatically judging the acceptability of a filter as to its perfection by checking whether the pressure at the primary side of the membrane filter is within a specified judging range at a predetermined time after the start of pressure increase at the primary side of the membrane filter by the gas.

2. The membrane filter testing apparatus as claimed in claim 1, wherein the valve is a needle valve.

3. The membrane filter testing apparatus as claimed in claim 1, wherein the circuit structured and arranged for controlling the gas pressure is also structured and arranged to interrupt the increase of pressure for a predetermined period of time upon the primary-side pressure reaching a predetermined level lower than a lower limit of the judging range, and checks whether the primary-side pressure decreases during the interruption.

* * * * *